US007629295B2

(12) United States Patent
Wienhues et al.

(10) Patent No.: US 7,629,295 B2
(45) Date of Patent: *Dec. 8, 2009

(54) DETERMINATION OF A SPECIFIC IMMUNOGLOBULIN USING MULTIPLE ANTIGENS

(75) Inventors: Ursula-Henrike Wienhues, Krailling (DE); Cornelia Kruse-Müller, Edewecht (DE); Eva Höss, Starnberg (DE); Elke Faatz, Pähl (DE); Beatus Ofenloch-Hähnle, Wielenbach (DE); Christoph Seidel, Weilheim (DE); Michael Wiedmann, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 340 days.

This patent is subject to a terminal disclaimer.

(21) Appl. No.: 10/613,018

(22) Filed: Jul. 7, 2003

(65) Prior Publication Data

US 2005/0074750 A1    Apr. 7, 2005

Related U.S. Application Data

(62) Division of application No. 08/776,188, filed as application No. PCT/EP95/02919 on Jul. 24, 1995, now Pat. No. 6,613,530.

(30) Foreign Application Priority Data

Jul. 25, 1994    (DE) ............................... P 44 26 276
Aug. 31, 1994    (DE) ............................... P 44 30 972

(51) Int. Cl.
  *C40B 30/04*    (2006.01)
  *G01N 33/53*    (2006.01)
  *A61K 38/00*    (2006.01)
  *C12P 21/08*    (2006.01)
(52) U.S. Cl. ........................... 506/9; 435/7.1; 530/300; 530/387.1
(58) Field of Classification Search .................... 506/9; 435/7.1; 530/300, 387.1
  See application file for complete search history.

(56) References Cited

U.S. PATENT DOCUMENTS 5,437,983 A * 8/1995 Watts et al. ............... 435/7.5
5,618,533 A * 4/1997 Flavell et al. ............. 424/184.1
6,613,530 B1 * 9/2003 Wienhues et al. .......... 435/7.1

FOREIGN PATENT DOCUMENTS

| CA | 2053924 | | 10/1990 |
|---|---|---|---|
| CA | 2182889 A1 | | 8/1995 |
| CA | 2116764 | | 12/1999 |
| EP | 0 507 586 | * | 4/1992 |
| EP | 0 507 586 A2 | | 10/1992 |
| JP | 02-290554 | | 11/1990 |
| JP | 03-089163 | | 4/1991 |
| JP | 03-089164 | | 4/1991 |
| JP | 03-089165 | | 4/1991 |
| WO | WO 88/09933 A1 | | 12/1988 |
| WO | WO9007119 | * | 6/1990 |
| WO | WO 93/16199 A1 | | 8/1993 |

OTHER PUBLICATIONS

Hashida et al., Diagnosis of HIV-1 Infection by Detection of Antibody IgG to HIV-1 in Urine with Ultrasensitive Enzyme Immunoassay (Immune Complex Transfer Enzyme Immunoassay) Using Recombinant Proteins as Antigens, 1994, Journal of Clinical Laboratory Analysis, 8(4): 237-246.*
Hoesel et al., 2004, Development and evaluation of a new ELISA for the detection and quantification of antierythropoietin antibodies in human sera, Journal of Immunological Methods, 294: 101-110.*
Chersi A. et al., "Aims and Limitations in the Use of Antipeptide Antibodies in Molecular Biology" *Biol. Chem.*, 1997, vol. 378, pp. 635-640, XP008018753.
Posnett D. N. et al., "A Novel Method for Producing Anti-Peptide Antibodies" *The Journal of Biological Chemistry*, 1988, vol. 263, No. 4, pp. 1719-1725, XP002070408.
Tam J. P., "Synthetic Peptide Vaccine Design: Synthesis and Properties of a High-Density Multiple Antigenic Peptide System" *Proc. Natl. Acad. Sci. USA*, 1988, vol. 85, pp. 5409-5413, XP002070407.

* cited by examiner

*Primary Examiner*—Amber D. Steele
(74) *Attorney, Agent, or Firm*—Rothwell, Figg, Ernst & Manbeck, P.C.

(57) ABSTRACT

The invention concerns a method for the immunological determination of a specific antibody in a sample liquid in which the sample liquid is incubated in the presence of a solid phase with two antigens directed against the antibody to be determined of which the first antigen carries at least one marker group and the second antigen is (a) bound to the solid phase or (b) is present in a form capable of binding to the solid phase and the antibody to be determined is detected by determining the marker group in the solid phase or/and in the liquid phase characterized in that at least one of the two antigens contains several epitope regions which react with the antibody to be determined.

18 Claims, 3 Drawing Sheets

Fig.1

Figure 3:
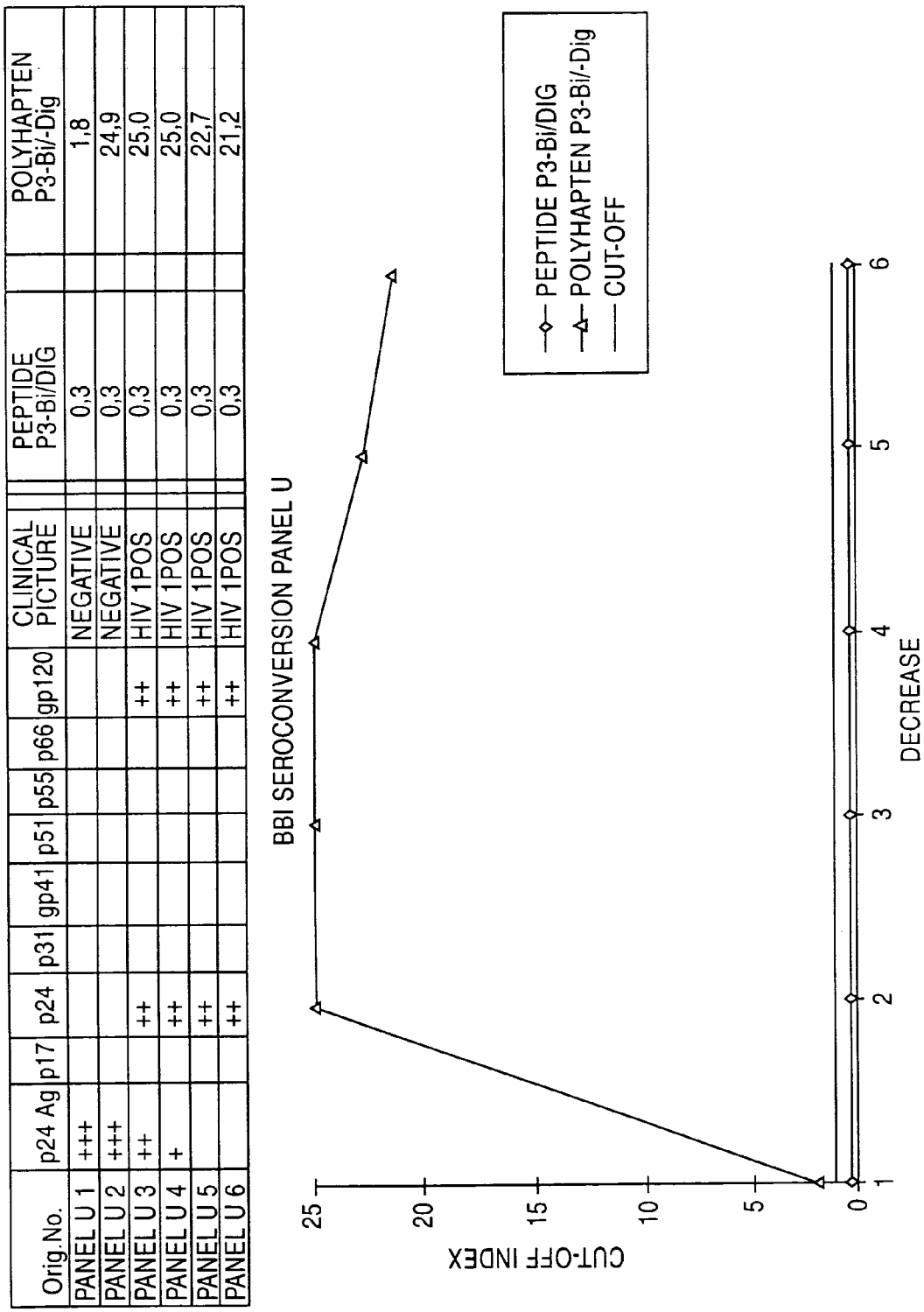

```
SEQUENCE REC. p24
  1   MTMITPSLAA   GPDKGNSSQV   SQNYPIVQNL   QGQMVHQAIS   PRTLNAWVKV   IEEKAFSPEV
                   | p17 (12aa) |           | -- >       p24 (231aa)
 61   IPMFSALSEG   ATPQDLNTML   NTVGGHQAAM   QMLKETINEE   AAEWDRVHPV   HAGPIAPGQM
121   REPRGSDIAG   TTSTLQEQIG   WMTNNPPIPV   GEIYKRWIIL   GLNKIVRMYS   PVSILDIRQG
181   PKEPFRDYVD   RFYKTLRAEQ   ASQEVKNWMT   ETLLVQNANP   DCKTILKALG   PAATLEEMMT
241   ACQGVGGPGH   KARVLAEAMS   QVTNSATIMM   QRGNFRNQKK   TVKCFNCGKE   GHIAKNCRAP
                   < --        |           p15 (72aa)
301   RKKGCWKCGK   EGHQMKDCTE   RQANFLGN
                                           LINKER (1aa)
```

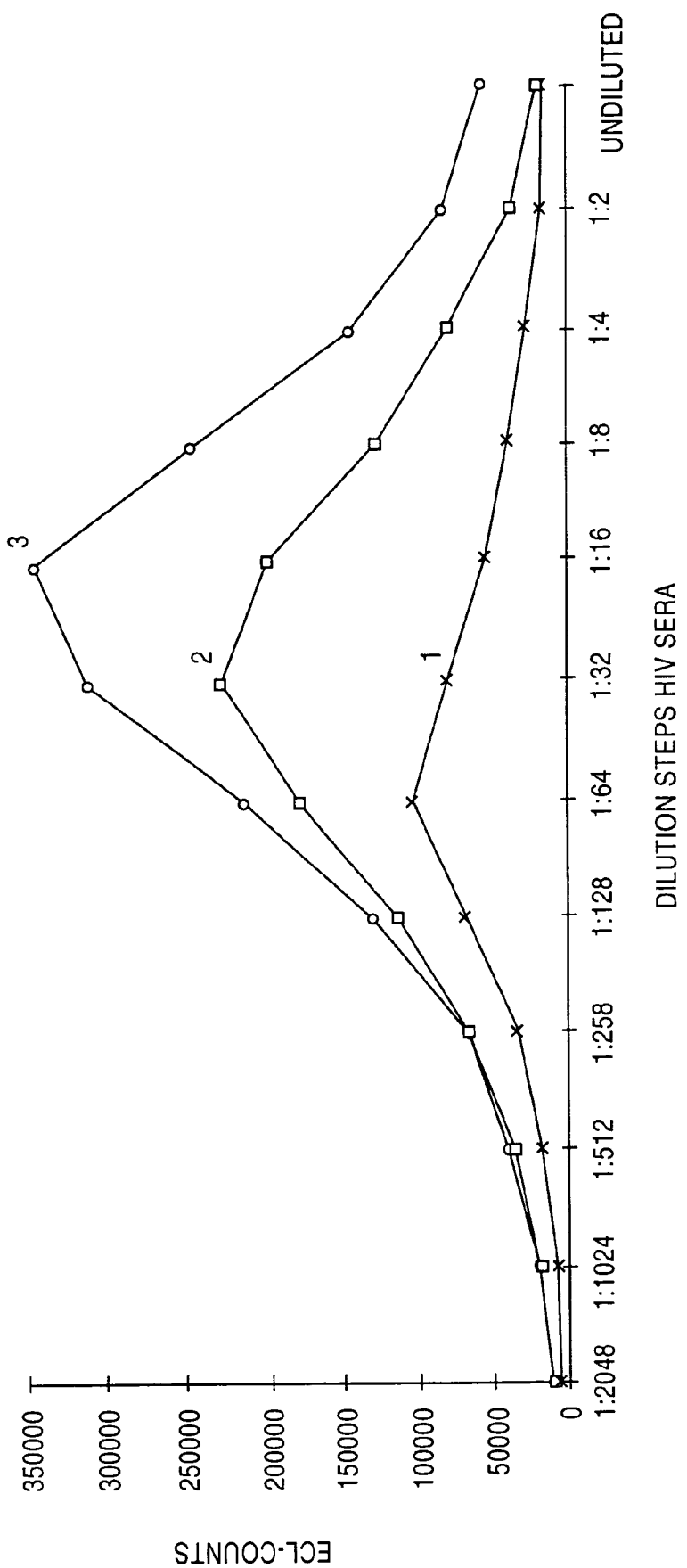

SEQUENCE LISTING

```
<160> NUMBER OF SEQ ID NOS: 77

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 1

Asn Asn Thr Arg Lys Ser Ile Ser Ile Gly Pro Gly Arg Ala Phe Tyr
  1               5                  10                  15

Thr

<210> SEQ ID NO 2
<211> LENGTH: 16
<212> TYPE: PRT
```

```
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 2

Asn Thr Thr Arg Ser Ile Ser Ile Gly Pro Gly Arg Ala Phe Tyr Thr
 1               5                  10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 3

Ile Asp Ile Gln Glu Glu Arg Arg Met Arg Ile Gly Pro Gly Met Ala
 1               5                  10                  15

Trp Tyr Ser

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 4

Gln Ala Arg Ile Leu Ala Val Glu Arg Tyr Leu Lys Asp Gln Gln Leu
 1               5                  10                  15

Leu Gly Ile Trp Gly Ala Ser Gly
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 5

Leu Gly Ile Trp Gly Cys Ser Gly Lys Leu Ile Cys Thr Thr Ala Val
 1               5                  10                  15

Pro Trp Asn Ala Ser Trp Ser
            20

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 6

Lys Asp Gln Gln Leu Leu Gly Ile Trp Gly Ser Ser Gly Lys Leu
 1               5                  10                  15

<210> SEQ ID NO 7
<211> LENGTH: 15
<212> TYPE: PRT
<213> ORGANISM: Artificial Sequence
```

```
<220> FEATURE:
<223> OTHER INFORMATION: Description of Artificial Sequence: Epitope
      region of HIV type 1, HIV type 2 or

```
<400> SEQUENCE: 12

Pro Gln Asp Val Lys Phe Pro Gly Gly Gly Gln Ile Val Gly Gly Val
 1               5                  10                  15

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Epitope
      region of Hepatitis C Virus

<400> SEQUENCE: 13

Glu Glu Ala Ser Gln His Leu Pro Tyr Ile Glu Gln
 1               5                  10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Epitope
      region of Hepatitis C Virus

<400> SEQUENCE: 14

Gln Lys Ala Leu Gly Leu Leu Gln Thr
 1               5

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Epitope
      region of Hepatitis C Virus

<400> SEQUENCE: 15

Ser Arg Gly Asn His Val Ser Pro Thr His Tyr Val Pro Glu Ser Asp
 1               5                  10                  15

Ala Ala

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Epitope
      region of Hepatitis C Virus

<400> SEQUENCE: 16

Pro Gln Arg Lys Asn Lys Arg Asn Thr Asn Arg Arg Pro Gln Asp Val
 1               5                  10                  15

Lys Phe Pro Gly Gly Gly Gln Ile Val Gly Gly Val
                20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Epitope
      region of Hepatitis C Virus

<400> SEQUENCE: 17

Ala Trp Tyr Glu Leu Thr Pro Ala Glu Thr Thr Val Arg Leu Arg Ala
 1               5                  10                  15
```

Tyr Met Asn Thr Pro Gly Leu Pro Val
            20                  25

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 18

Cys Xaa Xaa Xaa Trp Gly Ile Arg Gln Leu Arg Ala Arg Leu Leu Ala
 1               5                  10                  15

Leu Glu Thr Leu Leu Gln Asn
            20

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 19

Cys Xaa Xaa Xaa Leu Ser Leu Trp Gly Cys Lys Gly Lys Leu Val Cys
 1               5                  10                  15

Tyr Thr Ser

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES

```
<222> LOCATION: (4)
<223> OTHER INFORMATION: Beta-alanine

<400> SEQUENCE: 20

Cys Xaa Xaa Xaa Ala Leu Glu Thr Leu Leu Gln Asn Gln Gln Leu Leu
 1               5                  10                  15

Ser Leu Trp

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 21

Cys Xaa Xaa Xaa Ile Asp Ile Gln Glu Met Arg Ile Gly Pro Met Ala
 1               5                  10                  15

Trp Tyr Ser

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 22

Xaa Xaa Xaa Xaa Asn Asn Thr Arg Lys Ser Ile Ser Ile Gly Pro Gly
 1               5                  10                  15

Arg Ala Phe Tyr Thr
                20

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 23

Xaa Xaa Xaa Asn Thr Thr Arg Ser Ile Ser Ile Gly Pro Gly Arg Ala
 1               5                  10                  15

Phe Tyr

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 24

Xaa Xaa Xaa Xaa Ile Asp Ile Gln Glu Glu Arg Arg Met Arg Ile Gly
 1               5                  10                  15

Pro Gly Met Ala Trp Tyr Ser
            20

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 25
```

-continued

```
Xaa Xaa Xaa Xaa Ala Val Glu Arg Tyr Leu Lys Asp Gln Gln Leu Leu
 1               5                   10                  15

Gly Ile Trp

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Epsilon-aminocaproic acid
<220> FEATURE:
<221> NAME/KEY: MOD_RES
<222> LOCATION: (3)
<223> OTHER INFORMATION: Beta-alanine
<220> FEATURE:
<221> NAME/KEY: MOD_RES
<222> LOCATION: (4)
<223> OTHER INFORMATION: Epsilon-aminocaproic acid
<220> FEATURE:
<221> NAME/KEY: MOD_RES
<222> LOCATION: (5)
<223> OTHER INFORMATION: Beta-alanine

<400> SEQUENCE: 26

Xaa Xaa Xaa Xaa Xaa Ala Val Glu Arg Tyr Leu Lys Asp Gln Gln Leu
 1               5                   10                  15

Leu Gly Ile Trp
            20

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 27

Xaa Xaa Xaa Gln Ala Arg Ile Leu Ala Val Glu Arg Tyr Leu Lys Asp
 1               5                   10                  15

Gln Gln Leu Leu Gly Ile Trp Gly Ala Ser Gly
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Epsilon-aminocaproic acid

<400> SEQUENCE: 28

Xaa Xaa Gly Gly Gly Gly Gln Ala Arg Ile Leu Ala Val Glu Arg Tyr
  1               5                  10                  15

Leu Lys Asp Gln Gln Leu Leu Gly Ile Trp Gly Ala Ser
             20                  25

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 29

Xaa Xaa Xaa Xaa Trp Gly Ile Arg Gln Leu Arg Ala Arg Leu Leu Ala
  1               5                  10                  15

Leu Glu Thr Leu Leu Gln Asn
             20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 30

Xaa Xaa Xaa Xaa Leu Gly Ile Trp Gly Cys Ser Gly Lys Leu Ile Cys
```

```
                1               5                  10                 15
Thr Thr Ala Val
            20

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Digoxigenin-3-cme

<400> SEQUENCE: 31

Leu Gly Ile Trp Gly Cys Ser Gly Lys Xaa Leu Ile Cys Thr Thr Ala
  1               5                  10                  15
Val

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine
<220> FEATURE:
<221> NAME/KEY: MOD_RES
<222> LOCATION: (14)
<223> OTHER INFORMATION: Digoxigenin-3-cme

<400> SEQUENCE: 32

Xaa Xaa Xaa Xaa Leu Gly Ile Trp Gly Cys Ser Gly Lys Xaa Leu Ile
  1               5                  10                  15
Cys Thr Thr Ala Val
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Epsilon-aminocaproic acid
<220> FEATURE:
```

```
<221> NAME/KEY: MOD_RES
<222> LOCATION: (3)
<223> OTHER INFORMATION: Beta-alanine

<400> SEQUENCE: 33

Xaa Xaa Xaa Gly Cys Ser Gly Lys Leu Ile Cys Thr Thr Ala Val Pro
 1               5                  10                  15

Trp Asn Ala Ser Trp Ser
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Digoxigenin-3-cme

<400> SEQUENCE: 34

Gly Cys Ser Gly Lys Xaa Leu Ile Cys Thr Thr Ala Val Pro Trp Asn
 1               5                  10                  15

Ala Ser Trp Ser
            20

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)
<223> OTHER INFORMATION: Digoxigenin-3-cme

<400> SEQUENCE: 35

Gly Cys Ser Gly Lys Leu Ile Cys Thr Thr Ala Val Pro Trp Asn Ala
 1               5                  10                  15

Ser Trp Ser Lys Xaa Gly
            20

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine
```

```
<400> SEQUENCE: 36

Xaa Xaa Xaa Xaa Leu Ser Leu Trp Gly Cys Lys Gly Lys Leu Val Cys
 1               5                  10                  15

Tyr Thr Ser

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 37

Xaa Xaa Xaa Xaa Lys Asp Gln Gln Leu Leu Gly Ile Trp Gly Ser Ser
 1               5                  10                  15

Gly Lys Leu

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 38

Xaa Xaa Xaa Xaa Ala Leu Glu Thr Leu Leu Gln Asn Gln Gln Leu Leu
 1               5                  10                  15

Ser Leu Trp

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Epsilon-aminocaproic acid

<400> SEQUENCE: 39

Xaa Xaa Asn Ser Trp Gly Cys Ala Phe Arg Gln Val Cys His Thr Thr
 1               5                  10                  15

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 40

Xaa Xaa Xaa Xaa Asn Asn Thr Arg Lys Ser Ile Ser Ile Gly Pro Gly
 1               5                  10                  15

Arg Ala Phe Tyr Thr
            20

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 41

Xaa Xaa Xaa Asn Thr Thr Arg Ser Ile Ser Ile Gly Pro Gly Arg Ala
 1               5                  10                  15

Phe Tyr

<210> SEQ ID NO 42
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu(ethyleneglycol)
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 42

Xaa Xaa Xaa Asn Thr Thr Arg Ser Ile Ser Ile Gly Pro Gly Arg Ala
 1               5                  10                  15

Phe Tyr

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 43

Xaa Xaa Xaa Xaa Ile Asp Ile Gln Glu Glu Arg Arg Met Arg Ile Gly
 1               5                  10                  15

Pro Gly Met Ala Trp Tyr Ser
                 20

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES -continued

```
<222> LOCATION: (4)
<223> OTHER INFORMATION: Beta-alanine

<400> SEQUENCE: 44

Xaa Xaa Xaa Xaa Ala Val Glu Arg Tyr Leu Lys Asp Gln Gln Leu Leu
 1               5                  10                  15

Gly Ile Trp

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine

<400> SEQUENCE: 45

Xaa Xaa Gly Gly Gly Gln Ala Arg Ile Leu Ala Val Glu Arg Tyr Leu
 1               5                  10                  15

Lys Asp Gln Gln Leu Leu Gly Ile Trp Gly Ala Ser Gly
                20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu

<400> SEQUENCE: 46

Xaa Gly Gly Gly Gly Gln Ala Arg Ile Leu Ala Val Glu Arg Tyr Leu
 1               5                  10                  15

Lys Asp Gln Gln Leu Leu Gly Ile Trp Gly Ala Ser Gly
                20                  25

<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
```

<223> OTHER INFORMATION: Beta-alanine

<400> SEQUENCE: 47

Xaa Xaa Xaa Xaa Trp Gly Ile Arg Gln Leu Arg Ala Arg Leu Leu Ala
 1               5                  10                  15

Leu Glu Thr Leu Leu Gln Asn
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 48

Xaa Xaa Xaa Xaa Leu Gly Ile Trp Gly Cys Ser Gly Lys Leu Ile Cys
 1               5                  10                  15

Thr Thr Ala Val
            20

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine

<400> SEQUENCE: 49

Xaa Xaa Gly Gly Gly Gly Cys Ser Gly Lys Leu Ile Cys Thr Thr Ala
 1               5                  10                  15

Val Pro Trp Asn Ala Ser Trp Ser
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)

<223> OTHER INFORMATION: BPRu

<400> SEQUENCE: 50

Gly Cys Ser Gly Lys Leu Ile Cys Thr Thr Ala Val Pro Trp Asn Ala
1               5                   10                  15

Ser Trp Ser Lys Xaa
            20

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 51

Xaa Xaa Xaa Xaa Lys Asp Gln Gln Leu Leu Gly Ile Trp Gly Ser Ser
1               5                   10                  15

Gly Lys Leu

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 52

Xaa Xaa Xaa Xaa Ala Leu Glu Thr Leu Leu Gln Asn Gln Gln Leu Leu
1               5                   10                  15

Ser Leu Trp

<210> SEQ ID NO 53
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 53

Xaa Xaa Xaa Xaa Asn Ser Trp Gly Cys Ala Phe Arg Gln Val Cys His
  1               5                  10                  15

Thr Thr

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu

<400> SEQUENCE: 54

Xaa Gly Gly Gly Gln Ala Gln Leu Asn Ser Trp Gly Cys Ala Phe Arg
  1               5                  10                  15

Gln Val Cys His Thr Thr Val Pro Trp Pro Asn Asp Ser Leu Thr
             20                  25                  30

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 55

Cys Xaa Xaa Ser Arg Gly Asn His Val Ser Pro Thr His Tyr Val Pro
  1               5                  10                  15

Glu Ser Asp Ala Ala
             20

<210> SEQ ID NO 56
<211> LENGTH: 19
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 56

Xaa Xaa Xaa Xaa Ser Arg Arg Phe Ala Gln Ala Leu Pro Val Trp Ala
 1               5                  10                  15

Arg Pro Asp

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine

<400> SEQUENCE: 57

Xaa Xaa Pro Gln Asp Val Lys Phe Pro Gly Gly Gly Gln Ile Val Gly
 1               5                  10                  15

Gly Val

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)..(3)
<223> OTHER INFORMATION: Beta-alanine
<220> FEATURE:
<221> NAME/KEY: MOD_RES
<222> LOCATION: (4)
<223> OTHER INFORMATION: Epsilon-norleucine-OH

<400> SEQUENCE: 58

Xaa Xaa Xaa Xaa Glu Glu Ala Ser Gln His Leu Pro Tyr Ile Glu Gln
 1               5                  10                  15

<210> SEQ ID NO 59
<211> LENGTH: 12
```

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)..(3)
<223> OTHER INFORMATION: Beta-alanine

<400> SEQUENCE: 59

Xaa Xaa Xaa Gln Lys Ala Leu Gly Leu Leu Gln Thr
 1               5                  10

<210> SEQ ID NO 60
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 60

Xaa Xaa Xaa Xaa Ser Arg Gly Asn His Val Ser Pro Thr His Tyr Val
 1               5                  10                  15

Pro Glu Ser Asp Ala Ala
            20

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 61
```

```
Xaa Xaa Xaa Xaa Lys Asn Lys Arg Asn Thr Asn Arg Arg
 1               5                  10

<210> SEQ ID NO 62
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine

<400> SEQUENCE: 62

Xaa Xaa Pro Gln Arg Lys Asn Arg Asn Thr Asn Arg Arg Pro Gln Asp
 1               5                  10                  15

Val Lys Phe Pro Gly Gly Gly Gln Ile Val Gly Gly Val
                20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Digoxigenin-3-cme
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 63

Xaa Xaa Xaa Ala Trp Tyr Glu Leu Thr Pro Ala Glu Thr Thr Val Arg
 1               5                  10                  15

Leu Arg Ala Tyr Met Asn Thr Pro Gly Leu Pro Val
                20                  25

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu

<400> SEQUENCE: 64

Xaa Gly Gly Gly Gly Lys Asn Lys Arg Asn Thr Asn Arg Arg
 1               5                  10

<210> SEQ ID NO 65
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 65

Xaa Xaa Xaa Xaa Lys Asn Lys Arg Asn Thr Asn Arg Arg Pro Gln Asp
 1               5                  10                  15

Val Lys Phe Pro Gly Gly Gly Gln Ile Val Gly Gly Val
            20                  25

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine
<220> FEATURE:
<221> NAME/KEY: MOD_RES
<222> LOCATION: (15)..(16)
<223> OTHER INFORMATION: Epsilon-norleucine-OH

<400> SEQUENCE: 66

Xaa Xaa Xaa Xaa Ser Gln His Leu Pro Tyr Ile Glu Gln Gly Xaa Xaa
 1               5                  10                  15

Leu Ala Glu Gln Phe Lys Gln Gln Ala Leu Gly Leu Leu Gln Thr
            20                  25                  30

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
```

```
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 67

Xaa Xaa Xaa Ser Arg Gly Asn His Val Ser Pro Thr His Tyr Val Pro
 1               5                  10                  15

Glu Ser Asp Ala Ala
            20

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 68

Xaa Xaa Xaa Ser Arg Arg Phe Ala Gln Ala Leu Pro Val Trp Ala Arg
 1               5                  10                  15

Pro Asp

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 69

Xaa Xaa Xaa Lys Asn Lys Arg Asn Thr Asn Arg Arg Pro Gln Asp Val
 1               5                  10                  15

Lys Phe Pro Gly Gly Gly Gln Ile Val Gly Gly Val Leu Leu Pro Arg
            20                  25                  30

Arg

<210> SEQ ID NO 70
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 70

Xaa Xaa Xaa Asn Pro Lys Pro Gln Lys Lys Asn Lys Arg Asn Thr Asn
 1               5                  10                  15

Arg Arg

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 71

Xaa Xaa Xaa Gly Gln Ile Val Gly Gly Val Tyr Leu Leu Pro Arg Arg
 1               5                  10                  15

Gly Pro Arg Leu Gly
            20

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 72

Xaa Xaa Xaa Pro Gln Asp Val Lys Phe Pro Gly Gly Gly Gln Ile Val
 1               5                  10                  15

Gly Gly Val

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 73

Xaa Xaa Xaa Xaa Ser Arg Gly Asn His Val Ser Pro Thr His Tyr Val
 1               5                  10                  15

Pro Glu Ser Asp Ala Ala
            20

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid
<220> FEATURE:
<221> NAME/KEY: MOD_RES
<222> LOCATION: (4)
<223> OTHER INFORMATION: Beta-alanine

<400> SEQUENCE: 74

Xaa Xaa Xaa Xaa Ser Gln His Leu Pro Tyr Ile Glu Gln
 1               5                  10

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Epitope
      region of HIV type 1, HIV type 2 or HIV subtype O

<400> SEQUENCE: 75

Pro Gln Lys Lys Asn Lys Arg Asn Thr Asn Arg Arg Pro Gln Asp Val
 1               5                  10                  15

Lys Phe Pro Gly Gly Gly Gln Ile Val Gly Gly Val
            20                  25

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BPRu
<220> FEATURE:
<221> NAME/KEY: MOD_RES
<222> LOCATION: (2)
<223> OTHER INFORMATION: Beta-alanine
<220> FEATURE:
<221> NAME/KEY: MOD_RES
<222> LOCATION: (3)
<223> OTHER INFORMATION: Epsilon-aminocaproic acid

<400> SEQUENCE: 76

Xaa Xaa Xaa Asn Pro Lys Pro Gln Arg Lys Asn Lys Arg Asn Thr Asn
 1               5                  10                  15

Arg Arg

<210> SEQ ID NO 77
<211> LENGTH: 328
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Thr Met Ile Thr Pro Ser Leu Ala Ala Gly Pro Asp Lys Gly Asn
 1               5                  10                  15

Ser Ser Gln Val Ser Gln Asn Tyr Pro Ile Val Gln Asn Leu Gln Gly
            20                  25                  30

Gln Met Val His Gln Ala Ile Ser Pro Arg Thr Leu Asn Ala Trp Val
        35                  40                  45

Lys Val Ile Glu Glu Lys Ala Phe Ser Pro Glu Val Ile Pro Met Phe
    50                  55                  60

Ser Ala Leu Ser Glu Gly Ala Thr Pro Gln Asp Leu Asn Thr Met Leu
65                  70                  75                  80

Asn Thr Val Gly Gly His Gln Ala Ala Met Gln Met Leu Lys Glu Thr
                85                  90                  95

Ile Asn Glu Glu Ala Ala Glu Trp Asp Arg Val His Pro His His Ala
            100                 105                 110

Gly Pro Ile Ala Pro Gly Gln Met Arg Glu Pro Arg Gly Ser Asp Ile
        115                 120                 125

Ala Gly Thr Thr Ser Thr Leu Gln Glu Gln Ile Gly Trp Met Thr Asn
    130                 135                 140

Asn Pro Pro Ile Pro Val Gly Glu Ile Tyr Lys Arg Trp Ile Ile Leu
145                 150                 155                 160

Gly Leu Asn Lys Ile Val Arg Met Tyr Ser Pro Val Ser Ile Leu Asp
                165                 170                 175

Ile Arg Gln Gly Pro Lys Glu Pro Phe Arg Asp Tyr Val Asp Arg Phe
            180                 185                 190

Tyr Lys Thr Leu Arg Ala Glu Gln Ala Ser Gln Glu Val Lys Asn Trp

-continued

```
                195                 200                 205
Met Thr Glu Thr Leu Leu Val Gln Asn Ala Asn Pro Asp Cys Lys Thr
    210                 215                 220
Ile Leu Lys Ala Leu Gly Pro Ala Ala Thr Leu Glu Glu Met Met Thr
225                 230                 235                 240
Ala Cys Gln Gly Val Gly Gly Pro Gly His Lys Ala Arg Val Leu Ala
                245                 250                 255
Glu Ala Met Ser Gln Val Thr Asn Ser Ala Thr Ile Met Met Gln Arg
                260                 265                 270
Gly Asn Phe Arg Asn Gln Lys Lys Thr Val Lys Cys Phe Asn Cys Gly
            275                 280                 285
Lys Glu Gly His Ile Ala Lys Asn Cys Arg Ala Pro Arg Lys Lys Gly
        290                 295                 300
Cys Trp Lys Cys Gly Lys Glu Gly His Gln Met Lys Asp Cys Thr Glu
305                 310                 315                 320
Arg Gln Ala Asn Phe Leu Gly Asn
                325
```

DETERMINATION OF A SPECIFIC IMMUNOGLOBULIN USING MULTIPLE ANTIGENS

CROSS REFERENCE TO RELATED APPLICATION

This application is a divisional application of U.S. Ser. No. 08/776,188 filed Jan. 24, 1997 now U.S. Pat. No. 6,613,530, which is a 35 USC 371 National Phase Entry Application from PCT/EP95/02919, filed Jul. 24, 1995, and designating the U.S.

The present invention concerns a method for the determination of a specific immunoglobulin using antigens that comprise several epitope regions.

The detection of immunoglobulins in body fluids, in particular in human sera, is used to diagnose infections with microorganisms, in particular viruses, such as HIV, hepatitis viruses etc. The presence of specific immunoglobulins in the examined sample is usually detected by reaction with one or several antigens that react with the specific immunoglobulins. Methods for the determination of specific immunoglobulins in the sample liquid must be sensitive, reliable, simple and rapid.

In recent years more and more detection systems based on non-radioactive marker groups have been developed in which the presence of an analyte, e.g. a specific antibody, in the examined sample can be determined with the aid of optical (e.g. luminescence or fluorescence), NMR-active or metal-precipitating detection systems.

EP-A-0 307 149 discloses an immunological test for an antibody in which two recombinant polypeptides are used as antigens one of which is immobilized on a solid phase and the other carries a marker group and both recombinant antigens are expressed in different organisms to increase the specificity of the test.

EP-A-0 366 673 discloses a method for the detection of antibodies in a sample in which an antibody is detected by reaction with a purified labelled antigen and with the same purified antigen in a solid phase-bound form. Human IgG is for example disclosed as an antigen.

EP-A-0 386 713 describes a method for the detection of antibodies against HIV using two solid supports in which various HIV antigens are immobilized on the two solid supports each of which is brought into contact with an aliquot of a sample and with a labelled HIV antigen wherein the presence of antibodies is detected by a positive reaction in at least one of the tests. Recombinantly produced polypeptides are disclosed as HIV antigens.

EP-A-0 507 586 describes a method for carrying out an immunological test for a specific immunoglobulin in which a sample is brought into contact with two antigens capable of binding the immunoglobulin, wherein the first antigen carries a group suitable for binding to a solid support and the second antigen carries a marker group. The marker group can be a direct marker group e.g. an enzyme, a chromogen, a metal particle, or also an indirect marker group i.e. the marker group attached to the antigen can react with a receptor for the marker group which in turn carries a signal-generating group. A fluorescein derivative is mentioned as an example of such an indirect marker group, the receptor of which is an antibody which in turn is coupled to an enzyme. Polypeptides such as the hepatitis B surface antigen are disclosed as antigens. SH groups are introduced into this antigen by derivatization which are used to couple the fluorescein.

EP-A-0 507 587 discloses a specific method for the detection of IgM antibodies in which the sample is incubated with a labelled antigen which is directed against the antibody to be detected and with a second antibody which is also directed against the antibody to be detected and is capable of binding to a solid phase.

However, the immunological methods of detection according to the bridge test concept which are known from the state of the art in which a labelled antigen and an antigen capable of binding to a solid phase are used, still have major weaknesses. In particular they have a low sensitivity when a relatively low affinity is present between the antibody to be determined and the antigen. This is especially the case for a seroconversion that has occurred only recently and/or when new subtypes of the infectious microorganism occur. A further disadvantage of the previously known bridge test concepts is the risk of a false negative evaluation of high-titre samples due to the Hook effect.

The object of the present invention was therefore to provide a method for the detection of specific antibodies in which the disadvantages of the state of the art are at least partially eliminated and which has an adequate sensitivity especially in the case of a seroconversion which has only recently occurred and in the case of new microorganism subtypes. In addition the method according to the invention is intended to reduce the Hook effect.

This object is achieved by a method for the immunological determination of a specific antibody in a sample liquid in which the sample liquid is incubated in the presence of a solid phase with two antigens directed against the antibody to be determined in which the first antigen carries at least one marker group and the second antigen is (a) bound to the solid phase or (b) is present in a form capable of binding to the solid phase and the antibody to be determined is detected by determining the marker group in the solid phase or/and in the liquid phase characterized in that at least one of the two antigens comprises several epitope regions which react with the antibody to be determined.

Surprisingly it was found in bridge test immunoassays that the sensitivity of the test, especially for sera containing antibodies which have a low affinity for the antigen used, is improved by using at least one multimeric antigen i.e. an antigen with multiple epitope regions. In addition the method according to the invention leads to a considerable reduction of the risk of false negative evaluations of high-titre samples due to the Hook effect. The optimization of the antigen presentation by increasing the epitope density in the bridge test concept generally leads to an improvement in the reactivity with specific immunoglobulins in polyclonal sera as they occur in a sample liquid such as e.g. serum. A further advantage of the method according to the invention is that multimeric antigens have a considerably improved stability compared to monomeric antigens.

Two antigens are used in a method for the immunological determination of a specific antibody according to the bridge test concept. In a first preferred embodiment of the method according to the invention a multimeric antigen is used as the labelled antigen and a monomeric antigen is used as the solid phase antigen. In a second embodiment of the method according to the invention a multimeric antigen can be used as the solid phase antigen and a monomeric antigen can be used as the labelled antigen. In a third preferred embodiment multimeric antigens can be used as the labelled antigen and as the solid phase antigen.

The multimeric antigens contain multiple epitope regions i.e. structures, preferably peptide or polypeptide sequences, that react immunologically with the antibody to be determined. The epitope regions are preferably linked together via immunologically inactive regions e.g. via spacer regions. Multimeric antigens are preferably used which comprise several identical epitope regions.

The multimeric antigens according to the invention preferably contain more than 1 to 80 immunologically reactive epitope regions and particularly preferably more than 1 to 40 epitope regions. The epitope regions can be coupled to a high molecular carrier or linked together directly or via spacer regions.

The epitope regions are preferably immunologically reactive synthetic peptide sequences having a length of 6 to 50 amino acids or recombinant polypeptide sequences having a length of preferably up to 1000 amino acids. In addition to the actual epitope regions synthetic peptide epitopes preferably also contain a spacer region which for example can be used for coupling to other epitopes or to a carrier or/and for coupling marker groups or solid phase binding groups.

The spacer region is preferably an immunologically inactive peptide sequence having a length of 1 to 10 amino acids. The amino acids of the spacer region are preferably selected from the group comprising glycine, β-alanine, γ-aminobutyric acid, ε-aminocaproic acid, lysine and compounds of the structural formula $NH_2[(CH_2)_nO]_x—CH_2—CH_2—COOH$ in which n is 2 or 3 and x equals 1 to 10. The spacer region is preferably a continuous sequence of amino acids at the amino terminus or/and carboxy terminus of the epitope region.

In an immunoassay according to the bridge test concept a first labelled antigen is used. All marker groups can be used for the method according to the invention e.g. radioactive and non-radioactive marker groups. The preferred non-radioactive marker groups can be directly or/and indirectly detectable. In the case of a directly detectable label the group generating a detectable measuring signal is located directly on the antigen. Examples of such direct signal-generating groups are chromogens (fluorescent or luminescent groups, dyes), enzymes, NMR-active groups or metal particles which are coupled in a known manner to a peptide or polypeptide antigen. The directly detectable marker group is preferably a metal chelate detectable by fluorescence or electrochemoluminescence and particularly preferably a ruthenium chelate, rhenium chelate, iridium chelate or osmium chelate, especially a ruthenium chelate, e.g. a ruthenium-(bis-pyridyl)$_3^{2+}$ chelate. Other suitable metal chelate marker groups are for example described in EP-A-0 580 979, WO 90/05301, WO 90/11511 and WO 92/14138. Reference is hereby made to these documents.

A further type of labelling which is suitable for the antigens according to the invention is an indirectly detectable label. In this type of labelling the antigen is coupled with an indirectly detectable group e.g. a biotin or hapten group which in turn can be detected by reaction with a suitable binding partner (streptavidin, avidin, or anti-hapten antibody) which in turn carries a signal-generating group. An organic molecule with a molecular weight of 100 to 2000 preferably of 150 to 1000 is preferably used as an indirect marker group in the form of a hapten.

The haptens are capable of binding to a specific receptor for the respective hapten. Examples of receptors are antibodies, antibody fragments that are directed against the hapten or another specific binding partner for the hapten such as e.g. streptavidin or avidin if the hapten is biotin. The hapten is preferably selected from the group comprising sterols, bile acids, sexual hormones, corticoids, cardenolides, cardenolide-glycosides, bufadienolides, steroid-sapogenines and steroid alkaloids. The hapten is particularly preferably selected from the group comprising cardenolides and cardenolide-glycosides. Representatives of these substance classes are digoxigenin, digitoxigenin, gitoxigenin, strophanthidin, digoxin, digitoxin, ditoxin and strophanthin, digoxigenin and digoxin being particularly preferred. Another suitable hapten is for example fluorescein or a suitable fluorescein derivative.

The receptor for the hapten is coupled to a signal-generating group, preferably to an enzyme such as peroxidase, alkaline phosphatase, β-galactosidase, urease or Q-β-replicase. However, the signal-generating group can also be a chromogenic, radioactive or NMR-active group or a metal particle (e.g. gold). The hapten can for example be coupled to the antigen by coupling the hapten in the form of an active ester derivative to the amino terminus or/and to free amino side groups of the peptide or polypeptide antigen.

The term "active ester" within the sense of the present invention encompasses activated ester groups that can react with free amino groups of peptides under such conditions that no interfering side reactions with other reactive groups of the peptide can occur. An N-hydroxy-succinimide ester is preferably used as the active ester derivative. Examples of suitable hapten-active ester derivatives are digoxin-4'''-hemiglutarate-N-hydroxy-succinimide ester, digoxigenin-3-carboxymethyl ether-N-hydroxy-succinimide ester, digoxigenin-3-O-methyl-carbonyl-ε-aminocaproic acid-N-hydroxysuccinimide ester, digoxigenin-3-hemisuccinate-N-hydroxysuccinimide ester, digitoxin-4'''-hemiglutarate-N-hydroxysuccinimide ester and digitoxigenin-3-hemisuccinate-N-hydroxy-succinimide ester. These hapten derivatives are commercially available from the Boehringer Mannheim Company GmbH (Mannheim, GER). In addition to the N-hydroxysuccinimide esters it is also possible to use analogous p-nitro-phenyl, pentafluorophenyl, imidazolyl or N-hydroxybenzo-triazolyl esters.

In addition to the first labelled antigen a second antigen is also used in the method according to the invention which is bound to a solid phase or is present in a form capable of binding to a solid phase and can also be a multimeric antigen. Binding between the solid phase antigen and the solid phase can be covalent or adsorptive and occur directly, via chemical linker groups or via a specific interaction e.g. biotin-streptavidin/avidin, antigen-antibody, carbohydrate-lectin. The solid phase antigen is preferably a biotinylated antigen and the solid phase is correspondingly coated with streptavidin or avidin. Biotin groups can be coupled to the antigen in a known manner e.g. by introduction of biotin active ester derivatives. Such methods are known to a person skilled in the art.

The number of marker or solid phase binding groups on the multimeric antigen is variable i.e. one or several groups may be present. In some embodiments of the method according to the invention it is preferable if at least 3 and particularly preferably 3 to 20 marker or solid phase binding groups are present. In this manner it is possible to achieve a surprisingly high improvement in sensitivity and a significant decrease in the Hook effect (false negative evaluation of strongly positive samples).

The present invention is based on the finding that in an immunological test for the determination of a specific antibody in a sample liquid it is advantageous if at least one of the two antigens used for the test is a multimeric antigen i.e. comprises several epitope regions preferably several identical epitope regions. The term "epitope region" in the sense of the present invention denotes a structure, preferably a peptide or polypeptide sequence, which exhibits a specific reaction with the antibody to be determined. There are several possibilities of arranging several epitope regions on the multiple antigen.

In a first embodiment a carrier which does not react with the antibody to be determined to which the epitope regions are covalently coupled is used as the multimeric antigen.

Examples of suitable carriers are peptides, polypeptides or synthetic carriers e.g. dextrans. Examples of suitable polypeptides are albumins, e.g. bovine serum albumin, unspecific immunoglobulins, immunoglobulin fragments, β-galactosidase and polylysine. If a carrier is used care must be taken that it exhibits no cross-reactivity with antibodies in the sample liquid.

The epitope regions are preferably coupled via a bifunctional linker to reactive groups of the carrier e.g. $NH_2$ groups or SH groups. The coupling is preferably achieved via $NH_2$ groups of the carrier.

In this embodiment of the invention an antigen of the general formula $$(P—)_n T(—L)_m \quad\quad\quad (Ia)$$

or $$T(—P—L_m)_n \quad\quad\quad (Ib)$$

is preferably used in which T denotes a carrier, P denotes peptide or polypeptide sequences which contain identical or different immunologically reactive epitope regions and are covalently coupled to the carrier and L denotes marker groups or groups capable of binding to a solid phase which are covalently coupled to the carrier or to the peptide or peptide sequences, n is a number larger than 1 to 40 and m is a number between 1 and 10. The symbols n and m do not have to denote integers since the coverage of the carrier with epitope groups or with marker or solid phase binding groups can be statistical in a reaction mixture. n is preferably larger than or equal to 2.

The peptide or polypeptide sequences coupled to the carrier preferably contain synthetic peptide sequences with a length of 6 to 50 amino acids or recombinant polypeptide sequences with a length of preferably up to 1000 amino acids.

Synthetic peptide sequences can in addition to the actual epitope region also optionally contain a spacer region as defined above which can for example be located between the epitope and carrier or/and between the epitope and marker or solid phase binding group.

The peptide or polypeptide epitopes can be coupled to the carrier via the N-terminus, the C-terminus or via reactive groups in the side chain. One method of coupling is to activate an $NH_2$ group of the carrier molecule by reaction with known linker substances (e.g. maleinimidohexanoic acid, maleinimidopropionic acid, maleinimidobenzoic acid) and covalently couple an SH-activated peptide derivative to the carrier. The marker or solid phase binding groups are usually coupled to the carrier molecule or/and to the epitope regions in the form of active esters. However, other coupling methods are also conceivable e.g. via bifunctional photolinkers.

In order to synthesize multimeric antigens which contain the epitopes coupled to an inert carrier, the appropriate peptides are preferably synthesised with a reactive mercapto group e.g. by introducing an additional cysteine residue. In this case the peptide can be modified with a linker either N-terminally, C-terminally or also at any position in the sequence. For the reaction to form the multimeric antigen a carrier which contains primary amino groups can for example firstly be loaded with the appropriate active ester derivative of the marker group and subsequently with maleinimidoalkyl groups. In this manner the amino groups of the ε-amino side chain of lysine residues in the carrier are partially labelled with the marker group (e.g. digoxigenin or bipyridylruthenium) or the solid phase binding group (e.g. biotin) and the other portion is converted into maleinimide groups.

In a further step the peptide or the peptide mixture containing the desired epitope regions is then coupled to the maleinimide-modified carrier via the reactive mercapto function. If the marker group is located directly on the peptide, the multimeric antigen is synthesized in an analogous manner except that now an appropriately labelled SH-activated peptide is reacted with the carrier.

In a further embodiment of the invention a multimeric antigen can be used which contains several epitope regions which are covalently coupled together either directly or via spacer regions. The linking of the epitopes is preferably achieved at least partially via trifunctional linker molecules so that the antigen contains at least one branching site and preferably 1 to 7 branching sites.

In this embodiment an antigen of the general formula II is preferably used:

$$P^1\{P^2[P^3(P^4)_t]_s\}_r \quad\quad\quad (II)$$

in which $P^1$, $P^2$, $P^3$ and $P^4$ denote peptide sequences with a length of up to 50 amino acids in which at least 2 peptide sequences contain identical or different immunologically reactive epitope regions, r is 1 or 2, s is an integer from 0 to 4 and t is an integer from 0 to 8 wherein the antigen contains at least one branching site and at least one marker group or a group capable of binding to a solid phase.

The antigen of formula II forms a tree-like structure with a maximum of 7 branching sites if $P^1$, $P^2$, $P^3$ and $P^4$ are linear peptide sequences and preferably contains two to eight identical or different immunologically reactive epitope regions. The epitope regions are preferably not linked directly together but via spacer regions. The spacer regions are preferably immunologically inactive peptide sequences with a length of 1 to 10 amino acids as defined above. Not all peptide sequences $P^1$, $P^2$, $P^3$ and $P^4$ have to contain epitope regions, instead structures are also possible in which these sequences only consist of spacer regions. Branches can be incorporated into the structure by using trifunctional amino acids e.g. lysine or ornithine.

In addition the antigen of the general formula II contains at least one marker or solid phase binding group as defined above. These groups can for example be coupled selectively to the ends or/and to reactive side chains of the peptide sequences.

So-called mosaic proteins are yet a further embodiment of multimeric antigens i.e. recombinant fusion polypeptides whose amino acid sequence contains several immunologically reactive epitope regions which are optionally linked via immunologically inactive spacer regions. The recombinant mosaic proteins are obtainable by synthesizing a DNA sequence coding for the desired protein and expressing it in a recombinant host cell. Such procedures are known to a person skilled in the area of molecular biology and are described in standard textbooks (e.g. Sambrook et al., Molecular Cloning. A Laboratory Manual, 2nd Edition (1989), Cold Spring Harbor Laboratory Press). Marker or solid phase binding groups can also be introduced into the recombinant protein according to known methods.

In a further preferred embodiment of the invention the epitope regions are synthetic peptide sequences with a length of 6 to a maximum of 50 particularly preferably up to a maximum of 30 amino acids. Marker groups or solid phase binding groups can be selectively introduced into such epitope regions with regard to their location as well as with regard to their number. Thus in the synthetic production by using certain protecting groups on reactive side groups e.g. primary amino groups of the amino acid derivatives used it is possible to specifically select those positions of the peptide which are available for reaction with the introduced marker group after selective cleavage of the protecting group.

For this the peptide having the desired amino acid sequence is synthesized on a solid phase preferably using a commercial peptide synthesizer (e.g. the instruments A 431 or A 433 from Applied Biosystems). The synthesis is carried out according to known methods preferably starting at the carboxyl terminus of the peptide using amino acid derivatives. Amino acid derivatives are preferably used whose amino terminal groups required for coupling are derivatized with a fluorenylmethyloxycarbonyl (Fmoc) residue. Reactive side groups of the amino acids used contain protecting groups that can be readily cleaved off after completion of the peptide synthesis. Preferred examples of this are protecting groups such as triphenylmethyl (Trt), t-butyl ether (tBu), t-butyl ester (0 tBu), tert.-butoxycarbonyl (Boc) or 2,2,5,7,8-pentamethylchroman-6-sulfonyl (Pmc).

The amino side chains of lysine residues or of other amino acid derivatives with primary amino side groups that are located at positions of the peptide which are later intended to be derivatized with the hapten are provided with a first amino protecting group which is selected such that it can be quantitatively cleaved off under particular reaction conditions e.g. in the presence of acid. An example of a suitable acid-labile protecting group is Boc. The side groups of lysine residues or of other amino acid residues with primary amino side groups to which no coupling of a hapten is desired are provided with a second amino-protecting group which is selected such that it cannot itself be cleaved off under conditions under which the first protecting group can be cleaved off. The second protecting group is also preferably stable under those conditions under which the peptide is cleaved from the solid phase and under which all other protecting groups are cleaved off. Examples of such second protecting groups are acid-resistant protecting groups such as phenylacetyl. In addition to the 20 natural amino acids the peptide can also contain artificial amino acids such as β-alanine, γ-amino-butyric acid, ε-amino-caproic acid or norleucine. These artificial amino acids are used for the synthesis in a protected form analogously to the natural amino acids.

After completion of the synthesis protecting groups, including the first amino-protecting groups, which are located at the positions at which the coupling of the hapten is to take place are cleaved, optionally after releasing the peptide from the solid phase. Then the product obtained in this manner is purified, preferably by HPLC. Subsequently the hapten label is introduced by reacting the peptide with the hapten-active ester derivative desired in each case which reacts with free primary amino groups i.e. with the amino terminal group or/and amino side groups of the peptide. Preferably 1.5 to 2.5 equivalents of active ester are used per free primary amino group. Subsequently the reaction product is purified, preferably by HPLC.

If the peptide still contains amino groups that are derivatized with a second protecting group such as phenylacetyl then these protecting groups are removed in the last step. Phenylacetyl protecting groups can for example be enzymatically removed at room temperature with immobilized or soluble penicillin G amidase in aqueous solution containing an organic solvent.

If the peptides produced by the process according to the invention contain an intramolecular disulfide bridge, then the peptide sequence can be oxidized on the solid phase with for example iodine in hexafluoroisopropanol/dichloromethane (Cober et al. The Peptide, Academic Press, New York, 1981, pages 145 to 147) after completion of the synthesis but before cleaving the N-terminal Fmoc-protecting group of the last amino acid, and subsequently the N-terminal Fmoc-protecting group is cleaved.

A reactive SH group can for example be introduced by coupling a cysteine residue to the amino terminus of the peptide.

Metal chelate marker groups are introduced into synthetic peptides (a) after synthesis of the desired peptide sequence and preferably before cleavage of the peptide from the solid phase and before cleavage of protecting groups to reactive side groups of the amino acid derivatives used for the peptide synthesis by coupling an activated luminescent metal chelate e.g. an active ester derivative to the N-terminal primary amino group of the peptide and/or (b) during the synthesis of the peptide by introducing amino acid derivatives which are coupled covalently to a luminescent metal chelate marker group e.g. by means of a ε-derivatized lysine.

Branched multimeric antigens can be synthesized by using a diaminocarboxylic acid such as lysine protected by two Fmoc groups. The peptides can for example be biotinylated by introducing a biotin derivative at the N-terminus while the peptide is still coupled to the solid phase.

Peptide epitopes or polypeptide epitopes from pathogenic organisms e.g. bacteria, viruses and protozoa or from autoimmune antigens are preferably used for the method according to the invention. The immunologically reactive epitope region is preferably derived from viral antigens e.g. the amino acid sequences of HIV I, HIV II, HIV subtype O or hepatitis C-virus (HCV).

Preferably HIV I or HIV II or subtype O epitopes are selected from the regions gp32, gp41 gp120 and gp24. HCV epitopes are preferably selected from the Core/Env region or the non-structural protein regions NS3, NS4 or NS5.

The epitope region of HIV I or HIV II or HIV subtype O amino acid sequence is particularly preferable selected from the group of amino acid sequences:

```
NNTRKSISIG PGRAFYT           (I)    [SEQ ID NO: 1]

NTTRSISIGP GRAFYT            (II)   [SEQ ID NO: 2]

TDIQEERRMR IGPGMAWYS         (III)  [SEQ ID NO: 3]

QARILAVERY LKDQQLLGTW GASG   (IV)   [SEQ ID NO: 4]

LGIWGCSGKL TCTTAVPWNA SWS    (V)    [SEQ ID NO: 5]

KDQQLLGIWG SSGKL             (VI)   [SEQ ID NO: 6]

ALETLLQNQQ LLSLW             (VII)  [SEQ ID NO: 7]

LSLWGCKGKL VCYTS             (VIII) [SEQ ID NO: 8]

WGIRQLRARL LALETLLQN         (IX)   [SEQ ID NO: 9]

and

QAQLNSWGCA FRQVCHTTVP WPNDSLT (X)   [SEQ ID NO: 10]
``` or partial sequences thereof which have a length of at least 6 and preferably of at least 8 amino acids.

The amino acid sequences I to III are derived from the gp120 region of HIV I, the amino acid sequences IV to IX are derived from the gp41 region of HIV I and the amino acid sequence X is derived from the gp32 region of HIV II. The amino acid sequences I to X are also shown in the sequence protocols SEQ ID NO. 1 to SEQ ID NO. 10. Each of the sequences V, VIII and X contain two cysteine residues which are preferably present in the form of a disulfide bridge.

The epitope region of HCV amino acid sequences is preferably selected from the group of the amino acid sequences:

| | | |
|---|---|---|
| SRRFAQALPV WARPD | (XI) | [SEQ ID NO: 11] |
| PQDVKFPGGG QIVGGV | (XII) | [SEQ ID NO: 12] |
| EEASQHLPYI EQ | (XIII) | [SEQ ID NO: 13] |
| QKALGLLQT | (XIV) | [SEQ ID NO: 14] |
| SRGNHVSPTH YVPESDAA | (XV) | [SEQ ID NO: 15] |
| PQRKNKRNTN RRPQDVKF PG | (XVI) | [SEQ ID NO: 16] |
| GGQ IVGVV | and | |
| AWYELTPAET TVRLPAYMNT PGLPV | (XVII) | [SEQ ID NO: 17] | or partial sequences thereof which have a length of at least 6 and preferably at least 8 amino acids. The sequence XI is derived from the NS5 region, the sequences XII and XVI from the Core region, the sequences XIII, XIV and XV from the NS4 region and the sequence XVII is derived from the NS3 region of HCV. The amino acid sequences XI to XVII are also shown in the sequence protocols SEQ ID NO. 11 to SEQ ID NO. 17.

The present invention in addition concerns a reagent for the immunological determination of a specific antibody in a sample liquid comprising a reactive phase, two antigens directed against the antibody to be determined of which the first antigen carries a marker group and the second antigen is (a) bound to the solid phase or (b) is present in a form capable of binding to the solid phase characterized in that at least one of the two antigens contains several epitope regions which react to the antibody to be determined.

In one embodiment of the present invention the reagent contains a first labelled antigen with several epitope regions which carries at least one hapten marker group and a receptor for the hapten which in turn contains a signal-generating group. In addition a reagent is preferred which comprises a second solid phase antigen with several epitope regions which carries at least one biotin group and a reactive solid phase coated with streptavidin or avidin.

Yet a further subject matter of the present invention is the use of multimeric antigens which contains several immunologically reactive epitope regions in an immunological test procedure to determine specific antibodies in a sample liquid.

Those antibodies are preferably determined which indicate an infection by microorganisms such as bacteria, viruses or protozoa. Antibodies directed against viruses such as e.g. against HIV or hepatitis viruses are particularly preferably determined. The sample liquid is preferably serum, particularly preferably human serum. In addition it is preferred that the multimeric antigens according to the invention are used in an immunological method in a bridge test format.

The test procedure preferably comprises mixing the sample liquid with the first antigen and the second antigen on the solid phase in order to obtain a labelled immobilized complex of first antigen, antibody and solid phase-bound second antigen. Compared to other test formats for detecting antibodies, the bridge test format leads to an improvement in sensitivity i.e. all immunoglobulin classes such as IgG, IgM, IgA and IgE are recognized as well as in specificity i.e. the unspecific reactivity is reduced. The specificity and sensitivity of the double antigen bridge test can be further improved if a two step test procedure is used in which the sample liquid is mixed with the first and the second antigen in a first step and subsequently the receptor for the hapten label of the first antigen which carries the signal-generating group is added after 1 to 4 h, particularly preferably after 1.5 to 2.5 h.

The invention finally also concerns new antigens of formulae (Ia), (Ib) and (II) as defined above.

The present invention is further described by the following examples, sequence protocols and figures.

SEQ ID NO. 1: shows the amino acid sequence of an epitope from the gp120 region of HIV I;
SEQ ID NO. 2: shows the amino acid sequence of a further epitope from the gp120 region of HIV I;
SEQ ID NO. 3: shows the amino acid sequence of a further epitope from the gp120 region of HIV I, subtype O;
SEQ ID NO. 4: shows the amino acid sequence of an epitope from the gp41 region of HIV I;
SEQ ID NO. 5: shows the amino acid sequence of a further epitope from the gp41 region of HIV I;
SEQ ID NO. 6: shows the amino acid sequence of yet a further epitope from the gp41 region of HIV I;
SEQ ID NO. 7: shows the amino acid sequence of an epitope from the gp41 region of HIV I, subtype O;
SEQ ID NO. 8: shows the amino acid sequence of a further epitope from the gp41 region of HIV I, subtype O;
SEQ ID NO. 9: shows the amino acid sequence of yet a further epitope from the gp41 region of HIV I, subtype O;
SEQ ID NO. 10: shows the amino acid sequence of an epitope from the gp32 region of HIV II;
SEQ ID NO. 11: shows the amino acid sequence of an epitope from the NS5 region of HCV;
SEQ ID NO. 12: shows the amino acid sequence of an epitope from the Core region of HCV;
SEQ ID NO. 13: shows the amino acid sequence of an epitope from the NS4 region of HCV;
SEQ ID NO. 14: shows the amino acid sequence of a further epitope from the NS4 region of HCV;
SEQ ID NO. 15: shows the amino acid sequence of yet a further epitope from the NS4 region of HCV;
SEQ ID NO. 16: shows the amino acid sequence of a further epitope from the Core region of HCV and
SEQ ID NO. 17: shows the amino acid sequence of an epitope from the NS3 region of HCV;
FIG. 1: shows the amino acid sequence of the recombinant HIV p24 antigen, [SEQ ID NO: 77]
FIG. 2: shows a comparison of the measured signals in a double antigen bridge test when using a monomeric and a multimeric ruthenylated HIV-gp120 antigen and
FIG. 3: shows a comparison of the measured signals in a double antigen bridge test when using a monomeric and a multimeric biotinylated HIV-gp41 antigen.

EXAMPLE 1

Synthesis of Peptide Epitope Regions

The peptide epitope regions were synthesized by means of fluorenylmethyloxycarbonyl (Fmoc) solid phase peptide synthesis on a batch peptide synthesizer e.g. from Applied Biosystems A431 or A433. For this 4.0 equivalents of each of the amino acid derivatives shown in table 1 were used:

TABLE 1

| | |
|---|---|
| A | Fmoc-Ala-OH |
| C | Fmoc-Cys(Trt)-OH |
| D | Fmoc-Asp(tBu)-OH |
| E | Fmoc-Glu(tBu)-OH |
| F | Fmoc-Phe-OH |

TABLE 1-continued

| | |
|---|---|
| G | Fmoc-Gly-OH |
| H | Fmoc-His(Trt)-OH |
| I | Fmoc-Ile-OH |
| K1 | Fmoc-Lys(phenylacetyl)-OH |
| K2 | Fmoc-Lys(Boc)-OH |
| K3 | Fmoc-Lys(Fmoc)-OH |
| K4 | Fmoc-Lys(BPRu)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pmc)-OH |
| S | Fmoc-Ser(tBu)-OH |
| T | Fmoc-Thr(tBu)-OH |
| U | Fmoc-βAlanine-OH |
| V | Fmoc-Val-OH |
| W | Fmoc-Trp-OH |
| Y | Fmoc-Tyr(tBu)-OH |
| Z | Fmoc-ε-aminocaproic acid-OH |
| Nle | Fmoc-ε-norleucine-OH |
| Abu | Fmoc-γ-aminobutyric acid-OH |

If cysteine residues are present in the peptide sequence, an oxidation on the solid phase is carried out immediately after completion of the synthesis using iodine in hexafluoroisopropanol/dichloromethane.

The amino acids or amino acid derivatives were dissolved in N-methylpyrrolidone. The peptide was synthesized on 400-500 mg 4-(2',4'-dimethoxyphenyl-Fmoc-aminomethyl)-phenoxy resin (Tetrahedron Letters 28 (1987), 2107) with a loading of 0.4-0.7 mmol/g (JACS 95 (1973), 1328). The coupling reactions were carried out for 20 minutes in dimethylformamide as the reaction medium with 4 equivalents dicyclohexylcarbodiimide and 4 equivalents N-hydroxybenzotriazol relative to the Fmoc-amino acid derivative. The Fmoc group was cleaved within 20 minutes after each synthesis step using 20% piperidine in dimethylformamide.

The release of the peptide from the synthesis resin and the cleavage of the acid-labile protecting groups—with the exception of the phenylacetyl protecting group—was achieved within 40 min at room temperature with 20 ml trifluoro acetic acid, 0.5 ml ethanedithiol, 1 ml thioanisol, 1.5 g phenol and 1 ml water. The reaction solution was subsequently admixed with 300 ml cooled diisopropyl ether and kept at 0° C. for 40 min to completely precipitate the peptide. The precipitate was filtered, washed again with diisopropyl ether, dissolved in a small amount of 50% acetic acid and lyophilized. The crude material obtained was purified for ca. 120 min. by means of preparative HPLC on delta-PAK RP C18 material (column 50×300 mm, 100 Å, 15μ) using an appropriate gradient (eluant A: water, 0.1% trifluoro-acetic acid, eluant B: acetonitrile, 0.1% trifluoro-acetic acid). The identity of the eluted material was checked by means of ion spray mass spectrometry.

The hapten label, e.g. a digoxigenin or digoxin label, was introduced in solution by coupling appropriate active ester derivatives e.g. digoxigenin-3-carboxy-methylether-N-hydroxysuccinimide ester (Boehringer Mannheim GmbH, Mannheim, GER) to the free amino groups of the peptide. The peptide to be derivatized was dissolved in a mixture of DMSO and 0.1 M potassium phosphate buffer pH 8.5. Subsequently 2 equivalents of active ester per free primary amino function dissolved in a small amount of DMSO was added dropwise and stirred at room temperature. The reaction was monitored by means of analytical HPLC. The product is purified by means of preparative HPLC.

The lysine derivative K1 was used for positions at which no hapten labelling was to take place. The lysine derivative K2 was used for positions at which a hapten labelling was to take place. The lysine derivative K3 was used to couple the ε-amino group to the peptide in the spacer region.

If the peptide still contained lysines protected with phenylacetyl, then this protecting group was enzymatically cleaved at room temperature in the last step using penicillin G amidase in an aqueous medium containing a proportion of organic solvent. The enzyme was filtered and the peptide was purified by means of preparative HPLC. The identity of the eluted material was checked by means of ion spray mass spectrometry.

A ruthenium marker group was introduced either N-terminally by means of a ruthenium(bispyridyl)$_3$-carboxylic acid derivative (BPRu—COOH), e.g. Ru-(bispyridyl)$_3^{2+}$-N-hydroxysuccinimide ester or into the sequence by means of an ε-derivatized lysine residue K4 (Fmoc-Lys(BPRu)OH).

A biotin label was introduced either N-terminally by derivatization on a resin (biotin active ester) or within the sequence analogously to the introduction of a ruthenium label by means of a lysine appropriately ε-derivatized with biotin.

Branched multimeric peptides were synthesized analogously to the synthesis of the linear peptides. In this case a resin with a low loading density e.g. with a loading of 0.2 mmol/g was selected as the solid phase. A bis Fmoc-protected diamino carboxylic acid such as Fmoc-Lys(Fmoc)-OH was used for the branching.

The prepared peptides are listed in Tables 2 and 3.

The peptide compounds shown in Tables 2a-2d were prepared from the regions gp120, gp41 and gp32 of HIV I and HIV II.

TABLE 2A

SH-activated linear peptides

| | |
|---|---|
| gp41/1 | CUZU-WGIRQLRARLLALETLLQN [SEQ ID NO: 18] |
| gp41/2 | CUZU-LSLWGCKGKLVCYTS [SEQ ID NO: 19] |
| gp41/4 | CUZU-ALETLLQNQLLSLW [SEQ ID NO: 20] |
| gp120 | CUZU-IDIQEMRIGPMAWYS [SEQ ID NO: 21] |

TABLE 2b

Digoxigenin-labeled linear peptides

| | |
|---|---|
| gp120 | Digoxigenin-3-cme-UZU-NNTRKSISIGPGRAFYT [SEQ ID NO: 22] |
| | Digoxigenin-3-cme-UZ-NTTRSISIGPGRAFY [SEQ ID NO: 23] |
| | Digoxigenin-3-cme-UZU-IDIQEERRMRIGPGMAWYS [SEQ ID NO: 24] |
| gp41/1 | Digoxigenin-3-cme-UZU-AVERYLKDQQLLGIW [SEQ ID NO: 25] |
| | Digoxigenin-3-cme-ZUZU-AVERYLKDQQLLGIW [SEQ ID NO: 26] |
| | Digoxigenin-3-cme-UZ-QARILAVERYLKDQQLLGIWGASG [SEQ ID NO: 27] |
| | Digoxigenin-3-cme-ZGGGG-QARILAVERYLKDQQLLGIWGASG [SEQ ID NO: 28] |
| | Digoxigenin-3-cme-UZU-WGIRQLRARLLALETLLQN [SEQ ID NO: 29] |
| gp41/2 | Digoxigenin-3-cme-UZU-LGIWGCSGKLICTTAV [SEQ ID NO: 30] |
| | LGIWGCSGK-(cme-3-digoxigenin)-LICTTAV [SEQ ID NO: 31] |
| | Digoxigenin-3-cme-UZU-LGIWGCSGK-(cme-3-digoxigenin)-LICTTAV [SEQ ID NO: 32] |
| | Digoxigenin-3-cme-ZU-GCSGKLICTTAVPWNASWS [SEQ ID NO: 33] |
| | GCSGK-(cme-3-digoxigenin)-LICTTAVPWNASWS [SEQ ID NO: 34] |

TABLE 2b-continued

Digoxigenin-labeled linear peptides

| | |
|---|---|
| | GCSGKLICTTAVPWNASWSK (cme-3-digoxigenin) G [SEQ ID NO: 35] |
| | Digoxigenin-3-cme-UZU-LSLWGCKGKLVCYTS [SEQ ID NO: 36] |
| gp41/3 | Digoxigenin-3-cme-UZU-KDQQLLGIWGSSGKL [SEQ ID NO: 37] |
| gp41/4 | Digoxigenin-3-cme-UZU-ALETLLQNQLLSLW [SEQ ID NO: 38] |
| gp32 | Digoxigenin-3-cme-Z-NSWGCAFRQVCHTT [SEQ ID NO: 39] |

TABLE 2c

Ruthenylated linear peptides

| | |
|---|---|
| gp120 | BPRu-UZU-NNTRKSISIGPGRAFYT [SEQ ID NO: 40] |
| | BPRu-UZ-NTTRSISIGRGRAFY [SEQ ID NO: 41] |
| | BPRu-(ethyleneglycol)-UZ-NTTRSISIG PGRAFY [SEQ ID NO: 42] |
| | PBRu-UZU-IDIQEERRMRIGPGMAWYS [SEQ ID NO: 43] |
| gp41/1 | PBRu-UZU-AVERYLKDQQLLGIW [SEQ ID NO: 44] |
| | BPRu-UGGG-QARILAVERYLKDQQLLGIWGASG [SEQ ID NO: 45] |
| | BPRu-GGGG-QARILAVERYLKDQQLLGIWGASG [SEQ ID NO: 46] |
| | BPRu-UZU-WGIRQLRARLLALETLLQN [SEQ ID NO: 47] |
| gp41/2 | BPRu-UZU-LGIWGCSGKLICTTAV [SEQ ID NO: 48] |
| | BPRu-UGGG-GCSGKLICTTAVPWNASWS [SEQ ID NO: 49] |
| | (GCSGKLICTTAVPWNASWS)K-(BPRu) [SEQ ID NO: 50] |
| gp41/3 | BPRu-UZU-KDQQLLGIWGSSGKL [SEQ ID NO: 51] |
| gp41/4 | BPRu-UZU-ALETLLQNALLSLW [SEQ ID NO: 52] |
| gp32 | BPRu-UZU-NSWGCAFRQVCHTT [SEQ ID NO: 53] |
| | BPRu-GGG-QAQLNSWGCAFRQVCHTTVPWPNDSLT [SEQ ID NO: 54] |

TABLE 2d

Branched peptides

| | |
|---|---|
| gp120 | (NTTRSISIGPGRAFY-AbuZ AbuZ)$_2$-K-Z-AbuZ-K-(Bi) |
| | ((NTTRSISIGPGRAFY-ZU)$_2$-K-UU-K-(Bi) |
| | ((NNTRKSISIGPGRAFYT-UZU-K)$_2$-UZU-NNTRKSISIGPGRAFYT-UZU-K)$_2$-UZU-Bi |
| gp120 | (NTTRSISIGPGRAFY-ZU)$_2$-K-UU-K-(BPRu) |

The peptides shown in the following Tables 3a-d were synthesized from the NS5 region, the NS4 region, the Core region and the NS3 region of HCV.

TABLE 3a

SH-activated linear peptides

| | |
|---|---|
| NS4/3 | C-UZ-SRGNHVSPTHYVPESDAA [SEQ ID NO: 55] |

TABLE 3b

Hapten-labeled linear peptides

| | |
|---|---|
| NS5/1 | digoxigenin-3-cme-UZU-SRRFAQALPVWARPD [SEQ ID NO:56] |
| Core2m | digoxigenin-3-cme-U-PQDVKFPGGGQIVGGV [SEQ ID NO:57] |
| NS4/1 | digoxigenin-3-cme-UU-Nle-EEASQHLPYIEQ [SEQ ID NO:58] |
| NS4/2 | digoxigenin-3-cme-UU-QKALGLLQT [SEQ ID NO:59] |
| NS4/3 | digoxigenin-3-cme-UZU-SRGNHVSPTHYVPESDAA [SEQ ID NO:60] |

TABLE 3b-continued

Hapten-labeled linear peptides

| | |
|---|---|
| Core1 | digoxigenin-3-cme-UZU-KNKRNTNRR [SEQ ID NO:61] |
| Core1 + 2 | digoxigenin-3-cme-U-PQRKNKRNTNRRPQDVKFPGGGQI-VGVV [SEQ ID NO:62] |
| NS3/1 | digoxigenin-3-cme-UZ-AWYELTPAETTVRLRAYMNTP-GLPV [SEQ ID NO:63] |

| | |
|---|---|
| Core1 | BPRu-GGGG-KNKRNTNRR [SEQ ID NO:64] |
| Core1 + 2 | BPRu-UZU-KNKRNTNRRPQDVKFPGGGQIVGGV [SEQ ID NO:65] |
| NS4/1 + 2 | BPRu-UZU-SQHLPYIEQG-NleNle-LAEQFKQQALG-LLQT [SEQ ID NO:66] |
| NS4/3m | BPRu-UZ-SRGNHVSPTHYVPESDAA [SEQ ID NO:67] |
| NS5/1 | BPRu-UZ-SRRFAQALPVWARPD [SEQ ID NO:68] |
| Core1 + 2 + 3 | BPRz-UZ-KNKRNTNRRPQDVKFPGGGQIVGGVLL-PRR [SEQ ID NO:69] |
| Core1m | BPRu-UZ-NPKPQKKNKRNTNRR [SEQ ID NO:70] |
| Core3m | BPRu-UZ-GQIVGGVYLLPRRGPRLG [SEQ ID NO:71] |
| Core2m | BPRu-UZ-PQDVKFPGGGQIVGGV [SEQ ID NO:72] |
| NS4/3m-1 | BPRuz-UZU-SRGNHVSPTHYVPESDAA [SEQ ID NO:73] |
| NS4/1 | BPRu-UZU-SQHLPYIEQ [SEQ ID NO:74] |

TABLE 3d

Branched peptides

| | |
|---|---|
| NS4/3m | (SRGNHVSPTHYVPESDAA-UU)$_2$ KUUK (BPRu) |
| | (SRGNHVSPTHYVPESDAA-UU)$_4$ K$_2$KUUK (BPRu) |
| | (SRGNHVSPTHYVPESDAA-UU)$_8$ K$_4$U$_4$K$_2$KUUK (BPRu) |
| | (SRGNHVSPTHYVPESDAA-UU)$_2$ KUUK (Z-Bi) |
| | (SRGNHVSPTHYVPESDAA-UU)$_4$ K$_2$KUUK (Z-Bi) |
| | (SRGNHVSPTHYVPESDAA-UU)$_8$ K$_4$U$_4$K$_2$ KUUK (Z-Bi) |

EXAMPLE 2

Synthesis of Carrier-Bound Multimeric Antigens (Polyhaptens) with Peptide Epitopes The appropriate peptides were synthesized with a reactive mercapto function e.g. by introducing an additional cysteine (cf. Tables 2a and 2b). In this process the peptide can be modified with a so-called linker either N-, or C-terminally or at any desired position in the sequence. The corresponding peptides were synthesized as described in example 1.

For the reaction to form the polyhapten the carrier containing NH$_2$ groups was firstly loaded with the appropriate active ester of the marker groups and subsequently with maleinimidoalkyl groups, preferably by treatment with maleinimidohexyl- (MHS) or maleinimidopropyl-N-hydroxysuccinimide ester (MPS). By this means the primary amino groups in the carrier (e.g. ε-amino side chain of lysine residues) were partially labelled and the other part was converted into maleinimide groups.

The carrier was preferably reacted with the active esters in 0.1 mol/l potassium phosphate buffer pH 7.0-8.5 within 2-4 h at room temperature using a concentration of 5-20 mg/ml.

The lower molecular components were either separated by dialysis or gel chromatography (AcA 202-Gel, eluant 0.1 mol/l potassium phosphate buffer pH 7-8.5).

The peptide or the peptide mixture was then coupled within 6 h at room temperature in a further step with the reactive mercapto function on the MHS-modified labelled carrier in 0.1 mol/l potassium phosphate buffer pH 8.5. Non-reacted peptide was either separated by dialysis or gel chromatography.

If the label was to be located directly on the peptide, the polyhapten was synthesized analogously and an appropriately labelled SH-activated peptide was used.

Rabbit IgG, bovine serum albumin, β-galactosidase, amino-dextran and bovine Fab antibody fragments were used as carriers. The loading of the carrier with the peptide sequences was 1:2-1:20 on a molar basis. The loading of the carrier with marker groups was 1:1 to 1:20 on a molar basis.

EXAMPLE 3

Synthesis of Carrier-Bound Multimeric Antigens (Polyhaptens) Containing Polypeptide Epitopes as Exemplified by poly-p24-BSA-BPRu 1. Principle Bovine serum albumin (BSA) was reacted in the stated order with ruthenium-(bis-pyridyl)$_3^{2+}$-N-hydroxy-succinimide ester (BPRU) and maleinimidohexanoyl-N-hydroxysuccinimide ester (MHS) and dialysed in each case to separate the free, non-bound derivatization reagents.

Recombinant p24 antigen from *E. coli* (Ghrayeb and Chang, DNA5 (1986), 93-99) with the amino acid sequence shown in FIG. 1 was reacted with N-succinimidyl-S-acetylthio propionate (SATP) to introduce thiol residues via amino groups and dialysed to separate free non-bound SATP.

After releasing the SH groups in the activated p24 antigen it was coupled to the maleinimido functions of BSA-BPRu. Excess functional coupling groups were captured with cysteine and N-methylmaleinimide and the reaction was thus terminated.

The product was then isolated from the reaction mixture by chromatography on Sephacryl S 200.

2.1 Synthesis of BSA (MH)—BPRu

A 5-fold molar excess of BPRU reagent (0.4 ml BPRU stock solution containing 47 mg/ml in DMSO) was added to 250 mg BSA at a protein concentration of 20 mg/ml in PBS buffer pH 8.0.

After the addition it was stirred for a further 75 min at 25° C. The reaction was then stopped by addition of lysine to a final concentration of 10 mmol/l and stirred for a further 30 min at 25° C.

SH groups of BSA that are present were derivatized by addition of iodoacetamide to a final concentration of 10 mmol/l. For this purpose the mixture was stirred for a further 45 min at 25° C. and pH 8.0.

Free non-bound derivatization reagents were completely separated by dialysis (20 hours, 4° C.) against >500-fold volume of PBS buffer pH 7.5 (50 mmol/l Na phosphate, 150 mmol/l NaCl, pH 7.5).

The incorporation of BPRU was 4.7 moles per mole BSA. The yield was 220 mg BSA-BPRU (89%).

Then a 25-fold molar excess of MHS reagent (0.5 ml MHS stock solution containing 50 mg/ml in DMSO) was added to 220 mg BSA-BPRU at a protein concentration of 20 mg/ml in PBS buffer pH 7.1 and stirred for a further 60 min at 25° C.

The reaction was stopped by addition of lysine to a final concentration of 10 mmol/l and stirred for a further 30 min at 25° C.

Free non-bound MHS reagent was completely separated by dialysis (20 hours, 4° C.) against >500-fold volume PBS buffer pH 7.5. Yield: 210 mg BSA(MG)-BPRU (84%).

2.2 Synthesis of p24 Antigen (SATP)

A 3-fold molar excess of SATP reagent (0.06 ml SATP stock solution containing 35 mg/ml in DMSO) was added to 100 mg p24 antigen at a protein concentration of 10 mg/ml in 0.1 M Na phosphate, 0.1% (w/v) SDS, pH 7.1 and it was stirred for a further 60 min at 25° C.

The reaction was then stopped by addition of lysine to a final concentration of 10 mmol/l and stirred for a further 30 min at 25° C.

Free non-bound SATP reagent was subsequently completely separated by dialysis (20 hours, room temperature) against >500-fold volume 0.1 mol/l Na-phosphate, 0.1% (w/v) SDS, pH 6.5.

Yield: 95 mg p24 antigen (SATP) (95%).

2.3 Synthesis of poly-p24-Antigen BSA-BPRU

Hydroxylamine (1 mol/l; Merck) was added to a final concentration of 30 mmol/l to 95 mg p24 antigen (SATP) at a protein concentration of 10 mg/ml in 0.1 mol/l Na-phosphate, 0.1% (w/v) SDS, pH 7.5.

18 mg BSA(MH)—BPRU was added and the mixture was stirred for a further 60 min at a protein concentration of 9 mg/ml (pH 7.1; 25° C.). In order to stop the reaction cysteine was added to a final concentration of 2 mmol/l and stirred for a further 30 min at pH 7.1. N-methyl-maleinimide (Sigma) was subsequently added to a final concentration of 5 mmol/l and it was stirred for a further 30 min at pH 7.1 and 25° C.

The mixture stopped in this manner was dialysed for 18 hours at room temperature (RT) against >500-fold volume 0.1 mol/Na-phosphate, 0.1% (w/v) SDS, pH 6.5 and purified over a Sephacryl S 200 column (Pharmacia). The most important general conditions for the column operation are: column volume 340 ml, application volume 12 ml, flow rate: 13.0 cm/hour, mobile buffer 0.1 mol/l Na-phosphate, 0.1% (w/v) SDS, pH 6.5, operating temperature RT.

The column operation was monitored at a wavelength of 280 nm by means of a flow-through photometer and collected in fractions (fraction size about 0.5% of the column volume).

After UV recording the fractions of the high molecular elution profile were collected into a pool, the product was concentrated in an Amicon stirred cell with a YM30 membrane (Amicon) to a protein concentration of 10 mg/ml and frozen at −80° C.

Incorporation: 5 mole p24 antigen per mole p24 antigen-BSA-BPRU. Yield: 19 mg.

EXAMPLE 4

Improvement of the Sensitivity of the Bridge Test Format by Using Multimeric Antigens a) Carrier-Bound Multimeric Antigens (Polyhaptens)

Various variants of biotinylated polyhaptens were used in a double-antigen immunoassay in combination with a monomeric digoxygenylated hapten and namely with the same molar amount of biotinylated or digoxygenylated hapten. The amino acid sequence NNTRKSISIGPGRAFYT [SEQ ID NO: 1] from the gp120 region of HIV was used as the epitope. The haptens were synthesized as described in examples 1 and 2. The relative reactivity of native anti-HIV sera with the various biotinylated polyhaptens was standardized to the reactivity of sera with the corresponding biotinylated monomeric hapten (=100% reactivity).

The results of this experiment are shown in Table 4.

| Carrier molecule | Effective loading per carrier molecule | | Reactivity: compared to monomeric antigen (= 100%) |
|---|---|---|---|
| | biotin | peptide | |
| BSA (MW: 69000) | 1 | 4.2 | ca. 173.0% |
| (ca. 627 Aa) | 1 | 5.1 | ca. 185.0% |
| β-Gal (MW: 465000) | 1 | 2.2 | ca. 123.5% |
| (ca. 4227 Aa) | 1 | 3.6 | ca. 151.8% |
| | 1 | 9.4 | ca. 125.0% |
| Bovine-Fab (MW: 75000) | 1 | 5.9 | ca. 146.0% |
| (ca. 682 Aa) | | | | b) Multimeric Branched Antigens

Biotinylated and ruthenylated antigens with monomeric or multimeric branched epitopes were compared in a double antigen immunoassay in a bridge test format.

In the case of one epitope from the NS4 region of HCV (sequence SRGNHVSPTHYVPESDAA [SEQ ID NO: 15] the combination of a monomeric biotinylated antigen and a monomeric ruthenylated antigen was compared with the combination of multimeric branched biotinylated antigen (see Table 3d, line 2) and a monomeric ruthenylated antigen in a bridge test. The signal differentiation was determined i.e. the ratio in the measured signal between positive and negative samples. A higher signal differentiation means a better sensitivity. When using a multimeric biotinylated antigen a signal differentiation of 386 compared to a signal differentiation of only 208 for the combination of both monomeric antigens was obtained.

A double antigen bridge test was carried out correspondingly using an antigen sequence from the gp120 region of HIV. The epitope used has the amino acid sequence NTTRSISIGPGRAFY [SEQ ID NO: 2]. A combination of a monomeric biotinylated antigen and a monomeric ruthenylated antigen was compared with a combination of a multimeric branched biotinylated antigen (see Table 2d, line 2) and a multimeric ruthenylated antigen (see Table 2d, line 4). In a test using the combination of the two multimeric antigens a signal differentiation between a positive and negative sample of 12 was found. In contrast the combination of both monomeric antigens only has a signal differentiation of 10.

EXAMPLE 5

Improvement of the Sensitivity of the Bridge Test Format by Using Multimeric Carrier-Bound Antigens A combination of a monomeric biotinylated and a monomeric ruthenylated antigen, was examined in a bridge test together with a combination of a monomeric biotinylated antigen and a carrier-bound multimeric ruthenylated antigen (carrier molecule: bovine serum albumin; epitope: HIV-p24 antigen; produced according to example 3) and a combination of carrier-bound multimeric biotinylated antigen and a monomeric ruthenylated antigen. In two different positive samples (HIV sera) a signal differentiation positive/negative of 2 was found in each case with the combination of the two monomeric antigens whereas the combination of a monomeric biotinylated antigen and a multimeric ruthenylated antigen yielded a differentiation of 19 and 7 and the combination of the multimeric biotinylated antigen and a monomeric ruthenylated antigen yielded a differentiation of 4 and 3.

Even when using a combination of a monomeric biotinylated antigen and another multimeric ruthenylated antigen (carrier molecule: rabbit immunoglobulin) a much larger signal differentiation of positive/negative of 3, 22 and 10 was found in three different positive samples compared to 2, 9 and 8 for a combination of the monomeric antigens.

Even when using another epitope (recombinant protein from the HIV-gp41 region) it was possible to demonstrate the superiority of the multimeric antigens compared to the monomeric antigens. Whereas in the case of a combination of monomeric biotinylated and digoxigenylated antigens practically no differentiation between negative and positive was found in the bridge test, the combination of multimeric polyhaptens showed a very good differentiation.

EXAMPLE 6

Improvement of the Sensitivity of the Bridge Test Format by Using Multimeric Antigens A combination of an immobilized monomeric antigen and a labelled multimeric antigen is particularly preferred to achieve an optimal sensitivity over a broad concentration range of specific immunoglobulin. The preferred amounts used are 1 equivalent immobilized epitope to 0.2-10 and in particular 0.2-8 equivalents labelled epitopes.

FIG. 2 shows a comparison of a combination of a monomeric biotinylated antigen and a monomeric ruthenylated antigen in an epitope ratio of 1:1 (curve 1) and a combination of a monomeric biotinylated antigen and a multimeric ruthenylated carrier-bound antigen in an epitope ratio of 1:2 (curve 2) and 1:4 (curve 3).

The sequence stated in example 4a from the gp120 region of HIV was used as the epitope. The carrier molecule for the multimeric antigen was BSA. The loading of the carrier with epitope groups was 5:1 and 3:1 with the BPRu groups, each on a molar basis.

It is apparent from FIG. 2 that the use of multimeric antigens leads to a reduction of the Hook effect and to a general increase in the sensitivity.

EXAMPLE 7

Improvement of the Sensitivity of the Bridge Test Format when Using Multimeric Antigens by Increasing the Number of Marker Groups A further improvement of test sensitivity is achieved due to the fact that it is possible to increase the number of marker and solid phase binding groups to a large extent without masking the epitope regions or increasing the unspecific background values by increasing the hydrophobicity.

Digoxigenylated multimeric antigens were compared which contained epitopes from the gp120 region of HIV (cf example 4b) coupled to a bovine Fab antibody fragment carrier. In each case the carrier was loaded with the peptide epitope in the range of 1:6 to 1:7 on a molar basis. The loading of the carrier with digoxigenin groups was 1:2 and 1:4.

The results of this experiment are shown in Table 5. It can be seen that a non-linear improvement in sensitivity and a considerable reduction in the Hook effect was achieved by increasing the number of marker groups.

TABLE 5

| Sample | Stoichiometry carrier: Dig. 1:4 | Stoichiometry carrier: Dig. 1:2 |
|---|---|---|
| Dynamics of the measuring range | | |
| Dilution steps | mA | mA |
| 1/16384 | 36 | 148 |
| 1/8192 | 48 | 159 |
| 1/4096 | 49 | 151 |
| 1/2048 | 82 | 158 |
| 1/1024 | 132 | 159 |
| 1/512 | 302 | 157 |
| 1/256 | 675 | 164 |
| 1/128 | 1503 | 190 |
| 1/64 | 3493 | 259 |
| 1/32 | 7436 | 480 |
| 1/16 | 9306 | 1066 |
| 1/8 | 9449 | 3036 |
| 1/4 | 9449 | 3378 |
| 1/2 | 9449 | 2694 |
| undiluted | 9474 | 2266 |

EXAMPLE 8

Improvement of the Stability by Using Multimeric Antigens

The stability of monomeric and multimeric antigens was tested. For this purpose the signal recovery after a three day incubation at 35° C. relative to the original signal intensity was determined.

A signal recovery of 3.0 and 4.0% for two samples was determined for a monomeric ruthenylated antigen from the gp120 region of HIV (sequence see example 4) in combination with a fresh biotinylated monomeric antigen. When using a carrier-bound multimeric ruthenylated antigen (carrier: rabbit IgG, 4 marker groups and 3 epitopes per carrier molecule) a signal recovery of 73.1 and 73.6% was determined under the same test conditions.

A biotinylated monomeric antigen with the same epitope sequence was examined in a similar manner together with a carrier-bound biotinylated multimeric antigen (carrier: rabbit IgG, 18 biotin groups and 3 epitopes per carrier) in combination with a monomeric ruthenylated antigen. Signal recoveries of 25.0 and 37.0% were determined for the monomeric biotinylated antigen and 120.3 and 79.9% for the multimeric antigen.

EXAMPLE 9

Improvement of the Sensitivity with Respect to the Reactivity with Antigens of Low Affinity Multimeric antigens are preferably used to detect specific immunoglobulins of low affinity e.g. in the case of a recent seroconversion and in the case of new viral subtypes.

a) Ruthenylated Multimeric Antigens

The positive/negative signal differentiation was examined using antigens with an epitope sequence from the NS4/3 region of HCV. A combination of a monomeric ruthenylated and a monomeric biotinylated antigen resulted in a positive/negative signal differentiation of 3 and 1 in two different positive seroconversion samples i.e. a positive sample was not recognized as such. When multimeric IgG carrier-bound biotinylated and ruthenylated antigens were used a signal differentiation of 21 was determined in each case. Only the use of multimeric antigens enables the positive samples to be correctly classified.

b) Biotinylated Multimeric Antigens

The same peptide epitope from the gp41 region of HIV (gp41/3) was compared in each case as a carrier-bound multimeric antigen and as a monomeric antigen. In each case 50 ng/ml biotinylated and digoxigenylated monomeric peptide was used. In the case of the multimeric antigens 50 ng/ml "peptide equivalent" was used in which the amount of peptide was calculated from the degree of loading of the polyhapten. The test was carried out on an ES700 automated analyzer.

The test was carried out using various seroconversion panels as samples. FIG. 3 shows that the panels were correctly classified as positive in tests using the digoxigenylated polyhapten whereas a false negative result was obtained when using the monomeric antigen. The cut-off index is the boundary between negative and positive evaluation of an experiment. It is defined as the double value of the negative control.

We claim:

1. A method for detection of an antibody against a pathogenic organism in a liquid sample, wherein said pathogenic organism is selected from the group consisting of bacteria, virus and protozoan, the method comprising
   a) incubating
      (1) said liquid sample,
      (2) a solid phase,
      (3) a first antigen for said antibody, wherein the first antigen comprises multiple epitope regions, said epitope regions being identical in amino acid sequence and
      (4) a second antigen for said antibody, wherein the second antigen binds to the solid phase,
   under conditions to obtain a complex comprising a solid phase-bound second antigen to which is bound the antibody and to which is bound the first antigen; and
   b) detecting said antibody by direct or indirect detection of the complex on said solid phase, wherein said antibody is directed against said pathogenic organism; and
   wherein said first antigen is of formula (Ia) or (Ib)

$$(P{-})_n T({-}L)_n \qquad (Ia)$$

$$T({-}P{-}L_m)_n \qquad (Ib)$$

wherein
   T is a carrier,
   P is a peptide comprising an epitope region wherein said epitope region is reactive with the antibody,
   L is the marker group in said first antigen,
   is a covalent coupling,
   n is 2-40 and
   m is 1-10.

2. The method of claim 1, wherein P comprises at least one branching site of the formula $$P^1\{P^2[P^3(P^4)_t]_s\}_r$$

wherein
   $P^1$ through $P^4$ are each an amino acid sequence having a length of up to 50 amino acids wherein at least two of $P^1$ through $P^4$ comprise a copy of the single epitope and
   r is 1 or 2,
   s is an integer from 0 to 4 and
   t is an integer from 0 to 8,
   with the proviso that r, s and t are selected to result in P containing the at least one branching site and several copies of the single epitope.

3. The method according to claim 2, wherein the at least one branching site is formed by a trifunctional amino acid.

4. The method of claim 2, wherein the several copies of the single epitope are directly covalently coupled to each other or further comprise spacer regions which are covalently coupled between the conies such that the several copies are indirectly bound to each other via spacer regions.

5. The method according to claim 3, wherein the at least one branching site is formed by lysine, ornithine or both.

6. The method according to claim 1, wherein said second antigen is of formula (Ia) or (Ib)

$$(P{-})_n T({-}L)_n \qquad (Ia)$$

$$T({-}P{-}L_m)_n \qquad (Ib)$$

wherein
   T is a carrier,
   P is a peptide comprising an epitope region wherein said epitope region is reactive with the antibody,
   L is the marker group which binds to the solid phase in said second antigen,
   is a covalent coupling,
   n is 2-40 and
   m is 1-10.

7. The method of claim 1, wherein the second antigen comprises multiple epitope regions, said epitope regions being identical in amino acid sequence.

8. The method of claim 1, wherein said indirect detection of said antibody comprises:
   c) providing in step b) the first antigen wherein L comprises a hapten and a binding partner for the hapten being labeled with a signal generating group; and
   d) detecting the antibody by detecting the signal-generating group.

9. The method of claim 8, wherein the hapten is selected from the group consisting of a sterol, a bile acid, a sexual hormone, a corticoid, a cardenolide, a cardenolide-glycoside, a bufadienol, a steroid-sapogenine and a steroid alkaloid, and wherein the specific binding partner comprises an antibody for the hapten.

10. The method of claim 1, wherein the second antigen is biotinylated and the solid phase is coated with streptavidin or avidin.

11. The method of claim 1, wherein the carrier is non-reactive with the antibody.

12. The method of claim 11, wherein the carrier is a natural or synthetic peptide or polypeptide or a synthetic polysaccharide.

13. The method of claim 12, wherein the carrier is selected from the group consisting of an albumin, an immunoglobulin, an immunoglobulin fragment, a β-galactosidase, a polylysine and a dextran.

14. The method of claim 1, wherein P is a synthetic peptide sequence of 6 to 50 amino acids.

15. The method of claim 14, wherein the synthetic peptide sequence further comprises an immunologically inactive spacer region between epitope regions or between the epitope regions and the carrier.

16. The method of claim 1, wherein P is a recombinant polypeptide sequence comprising a length of up to 1000 amino acids, wherein the polypeptide sequence P comprises a single epitope region or a multiple, identical epitope regions.

17. The method of claim 1, wherein the first antigen and the second antigen is a recombinant fusion polypeptide wherein P is a mosaic peptide comprising multiples of immunologically reactive epitope regions.

18. The method according to claim 17, further comprising immunologically inactive spacer regions between said peptides (P).

* * * * *